United States Patent
Grassl et al.

(10) Patent No.: US 11,154,682 B2
(45) Date of Patent: Oct. 26, 2021

(54) VENTILATION TUBE UNIT FOR CONNECTION TO A MEDICAL VENTILATOR AS WELL AS A VENTILATION SYSTEM COMPRISING THE VENTILATOR AND AT LEAST ONE VENTILATION TUBE UNIT

(71) Applicant: Drägerwerk AG & Co. KGaA, Lübeck (DE)

(72) Inventors: Thomas Grassl, Lübeck (DE); Gerd Wotha, Warnsdorf (DE); Meinhard Braedel, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 1755 days.

(21) Appl. No.: 14/785,108

(22) PCT Filed: Feb. 21, 2014

(86) PCT No.: PCT/EP2014/000465
§ 371 (c)(1),
(2) Date: Oct. 16, 2015

(87) PCT Pub. No.: WO2014/169980
PCT Pub. Date: Oct. 23, 2014

(65) Prior Publication Data
US 2016/0074616 A1  Mar. 17, 2016

(30) Foreign Application Priority Data
Apr. 18, 2013 (DE) .................... 10 2013 006 780.4

(51) Int. Cl.
*A61M 16/08* (2006.01)
*A61M 39/10* (2006.01)

(52) U.S. Cl.
CPC .............. *A61M 16/0808* (2013.01); *A61M 16/0816* (2013.01); *A61M 16/0833* (2014.02);
(Continued)

(58) Field of Classification Search
CPC .............. A61M 16/00; A61M 16/0003; A61M 16/08; A61M 16/0808; A61M 16/0833;
(Continued)

(56) References Cited

U.S. PATENT DOCUMENTS

| 4,265,235 A | * | 5/1981 | Fukunaga | A61M 16/08 128/200.24 |
| 4,417,574 A | | 11/1983 | Talonn et al. | |
| 4,463,755 A | | 8/1984 | Suzuki | |

(Continued)

FOREIGN PATENT DOCUMENTS

| CN | 101856533 A | 10/2010 |
| CN | 102008776 A | 4/2011 |

(Continued)

*Primary Examiner* — Colin W Stuart
(74) *Attorney, Agent, or Firm* — McGlew and Tuttle, P.C.

(57) ABSTRACT

A ventilation tube unit (2), for connection to a medical ventilator, includes an outer tube (4) with a tubular connection device (18) with a jacket-side branch (24, 28), for connecting a medical unit such as a water trap, arranged between a first outer tube part (20) and a second outer tube part (22). An inner line (6) is arranged within and extends with the outer tube (4) between two port connectors (8). Each outer tube part (20, 22) includes a variable-length outer tube part that can be varied between a compressed state and an expanded state. The connection device (18) is displaceable in the longitudinal direction (A) relative to the inner line (6) by a compression of one outer tube part (20) and a corresponding expansion of the other outer tube part (22). A ventilation system with at least one such ventilation tube unit is also provided.

20 Claims, 2 Drawing Sheets

(52) U.S. Cl.
CPC .............. *A61M 16/0875* (2013.01); *A61M 2039/1083* (2013.01); *A61M 2205/21* (2013.01)

(58) Field of Classification Search
CPC .......... A61M 16/0816; A61M 16/0875; A61M 16/0883; A61M 39/00; A61M 39/08; A61M 39/10; A61M 39/105; A61M 2039/082; A61M 2205/21
See application file for complete search history.

(56) References Cited

U.S. PATENT DOCUMENTS

| | | | |
|---|---|---|---|
| 5,778,872 A * | 7/1998 | Fukunaga | A61M 16/1055 128/202.27 |
| 5,894,839 A * | 4/1999 | Rosenkoetter | A61M 16/08 128/200.24 |
| 6,880,957 B2 | 4/2005 | Walters | |
| 7,178,521 B2 | 2/2007 | Burrow et al. | |
| 7,870,857 B2 * | 1/2011 | Dhuper | A61M 16/08 128/203.12 |
| 8,156,935 B2 | 4/2012 | Chang | |
| 2004/0193101 A1 | 9/2004 | Van Hooser et al. | |
| 2005/0150505 A1 | 7/2005 | Burrow et al. | |
| 2006/0283447 A1 | 12/2006 | Dhuper et al. | |
| 2010/0122702 A1 | 5/2010 | Reinboth et al. | |
| 2010/0252035 A1 | 10/2010 | Chang | |
| 2010/0258129 A1 | 10/2010 | Huschke et al. | |

FOREIGN PATENT DOCUMENTS

| | | |
|---|---|---|
| DE | 32 18 771 A1 | 2/1983 |
| DE | 10 2008 057345 B3 | 4/2010 |
| EP | 1 352 670 A1 | 10/2003 |
| WO | 2006/127257 A2 | 11/2006 |

* cited by examiner

VENTILATION TUBE UNIT FOR CONNECTION TO A MEDICAL VENTILATOR AS WELL AS A VENTILATION SYSTEM COMPRISING THE VENTILATOR AND AT LEAST ONE VENTILATION TUBE UNIT

CROSS REFERENCE TO RELATED APPLICATIONS

This application is a United States National Phase application of International Application PCT/EP2014/000465 filed Feb. 21, 2014 and claims the benefit of priority under 35 U.S.C. § 119 of German Patent Application 10 2013 006 780.4 filed Apr. 18, 2013 the entire contents of which are incorporated herein by reference.

FIELD OF THE INVENTION

The present invention pertains to a ventilation tube unit for connection to a medical ventilator, comprising an outer tube with a tubular connection device, which has at least one jacket-side branch for connecting a medical unit, especially a water trap, and which is arranged between a first outer tube part and a second outer tube part of the outer tube, an inner line, which is arranged within the outer tube, and two port connectors, between which the outer tube and the inner line extend, wherein each port connector is connected by a corresponding inner line port to one end of the inner line and by a corresponding outer tube port to an end of the outer tube, which said end is located on the same side, and to a ventilation system with such a ventilation tube unit.

BACKGROUND OF THE INVENTION

Ventilators (also known as a respirators) as medical devices are used for the mechanical ventilation of human patients. The air is sent to the patient for the mechanical ventilation through a tube system. Condensation of humid air may occur in the ventilation system, especially in the ventilation tube unit connected to the medical ventilator, during the mechanical ventilation of the patient with the ventilator. The condensation water formed in this way leads to an increase in the air resistance in the ventilation tube unit or in the entire ventilation system and may even enter the patient's lungs during his mechanical ventilation. Water traps, which collect the condensation water formed in the ventilation tubes, so that the above-described hazards and risks do not occur any longer, are used to avoid this. Such water traps have a removable collection container, which is to be emptied at regular intervals.

The published patent application US 2010/0252035 A1 shows a ventilation tube unit for connection to a medical ventilator. The ventilation tube unit comprises an outer tube with an integrated T-distributor, at the end of which branching off from the outer tube, a water trap is connected for receiving water of condensation. Port connectors are provided on both sides of the outer tube in order to connect the ventilation tube unit to a medical ventilator, on the one hand, and to a connection piece of a ventilation mask or the like, on the other hand. The outer tube therefore extends between the two port connectors. Furthermore, an inner tube is provided, which is inserted into the outer tube in the manner of a coaxial arrangement. The inner tube is connected at its ends to the aforementioned port connectors. Thus, both the outer tube and the inner tube extend between the two port connectors. Such ventilation tube units for connection to a medical ventilator connect this to the port of a mask or the like at the patient. The ventilation tube unit usually hangs between the medical ventilator and the patient and forms an arc in its lateral contour. Condensation water, which is formed in the ventilation tube unit, usually flows to the deepest point of the arc formed by the ventilation tube unit due to gravity. Therefore, prior-art ventilation tube units make provisions for a water trap to be positioned in the middle between the port connectors. This is based on the assumption that the outer tube also sags at the deepest point in the middle between the port connectors, so that the condensation water is formed at this location and can be collected by the water trap.

It was, however, determined in practice that a ventilation tube unit between the medical device and the patient cannot always be arranged such that the water trap or the T-distributor is located at the deepest point of the outer tube. This may happen, for example, due to the fact that one port connectors of the ventilation tube unit is arranged higher than the opposite, second port connector. The deep point of the outer tube is off-center in the longitudinal direction. However, the condensation water collects at this off-center deep point. Based on the central arrangement of the water trap in the longitudinal direction, the water trap is not suitable for collecting the condensation water, so that the so-called resistance, i.e., the indicator of the flow resistance, as well as the so-called compliance, i.e., the indicator of the stretchability of the lumen, will change. Furthermore, there is a risk that the condensation water that has not been collected will reach the patient's lungs during his mechanical ventilation.

SUMMARY OF THE INVENTION

An object of the present invention is to provide a ventilation tube unit and a ventilation system, which can be adapted each during the operation such that the condensation water can be drained from the outer tube during the operation at any desired point of the outer tube, namely, possibly without changing the resistance and/or the compliance of the ventilation tube unit.

This object is accomplished by a ventilation tube unit for connection to a medical ventilator, comprising an outer tube with a tubular connection device, which has at least one jacket-side branch for connecting a medical unit, especially a water trap, and which is arranged between a first outer tube part and a second outer tube part of the outer tube, an inner line, which is arranged within the outer tube, and two port connectors, between which the outer tube and the inner line extend. Each port connectors is connected by an associated outer tube port to an end of the outer tube, which said end is located on the same side. Each outer tube part is designed as a variable-length outer tube part (a variable length structure) between a compressed (contracted) state and an expanded state, and the connection device can be displaced in the longitudinal direction relative to the inner line by compressing one outer tube part and correspondingly expanding the other outer tube part.

According to the present invention, the outer tube has a first outer tube part and a second outer tube part as well as a tubular connection device arranged between the outer tube parts with at least one jacket-side branch. The connection device may be, for example, a T-piece or a T-distributor or a Y-distributor. The outer tube may thus be fitted together from the outer tube parts and the connection device. However, as an alternative, the connection device may be an integral part of at least one of the outer tube parts and/or the outer tube may be made in one piece with integral connection device.

Both the outer tube and the inner line extend each between the port connectors according to the present invention. The port connectors have for this corresponding port connectors each for connection to the outer tube and the inner line.

According to the present invention, the inner line is arranged within the outer tube, so that a type of coaxial arrangement is preferably formed. It is guaranteed by this arrangement that at least one duct, which is used to circulate and/or deliver air within a ventilation circuit or ventilation system, is formed between the outer tube and the inner line.

In addition, provisions are made according to the present invention for each outer tube part to be designed as a variable-length outer tube part between a compressed state and an expanded state. Compression of the outer tube part in the longitudinal direction may be defined, for example, as compressing, pushing together, contracting, folding up or similar compaction of the outer tube in the longitudinal direction. Expansion of an outer tube part in the longitudinal direction is defined preferably as a change opposite to the above-mentioned compression of the outer tube part. Expansion of an outer tube part in the longitudinal direction may be, for example, stretching, pulling apart, unfolding and/or a similar expansion in the longitudinal direction.

The present invention is based on the discovery that when the outer tube parts undergo a corresponding change in length, this makes it possible to remove the condensation water from the outer tube at any desired point of the outer tube without changing the resistance and/or compliance of the duct defined by the outer tube, since the overall inner volume of the outer tube does not change due to the displacement of the connection device relative to the inner line, because this (outer tube) is arranged, just as the inner line, between the two port connectors. The length is preferably defined by the inner line, so that the overall length of the outer tube does not change due to the displacement of the connection device, either. Only the inner volume of one outer tube part and of the other outer tube part changes due to a displacement of the connection device, but it does so to an equal extent. If one outer tube part is reduced by a certain volume by a compression or pushing together, the other outer tube part increases by the same volume due to the corresponding expansion or pulling apart. When viewed from the outside, the outer tube has an at least essentially constant volume independently from the relative position of the connection device.

It is possible with the ventilation tube unit according to the present invention to position the connection device or the water trap, which can be connected to the aforementioned connection device, at the deepest (lowest) point of the outer tube. Even if the shape of the contour of the ventilation tube unit changes, for example, due to changing the position of the patient, the ventilation tube unit according to the present invention is set up to position the connection device or the water trap again at the new deepest point of the outer tube without opening the outer tube. The ventilation tube unit according to the present invention has the advantage that neither the compliance nor the resistance of the connection device is changed by the aforementioned adaptation. The settings of the medical ventilator can consequently be left unchanged. The hazards and risks of a mechanical ventilation of the lungs of a patient thus decrease markedly.

Provisions are made according to a preferred embodiment of the present invention for the outer tube to be longer in the fully pulled-out state than the inner line. The fact that the outer tube and the inner tube are mechanically coupled by the port connectors is left out of consideration here for the time being. The first outer tube part and the second outer tube part are preferably at least essentially as long, considered each in itself, in the fully pulled-out state as the inner line. It is thus possible that the connection device is displaceable approximately over the entire length of the ventilation tube unit relative to the inner line, since independently from the extent to which one of the two outer tube parts is pushed together, the other outer tube part is enabled to form the remainder of the outer tube by this remainder being pulled out to a corresponding extent. Provisions are made in an alternative variant for the first outer tube part and the second outer tube part to have, considered each in itself, at least 66% of the length of the inner line in the fully pulled-out state. This embodiment is based on the experience that even though the deep point of a ventilation tube unit used in practice cannot usually be found in the central position in the longitudinal position, it can often be found in the vicinity of the center. A flexible displacement of the connection device around the central area of the inner line may thus be sufficient for certain intended applications.

Provisions are made according to another, preferred embodiment of the present invention for the connection device to be compressed at one of plurality of resting positions between a first position, at which one outer tube part is compressed, and a second position, in which the other outer tube part is compressed, wherein the connection device maintains the respective resting position without the effect of external forces. Each of the two outer tube parts can be compressed to a certain length. The respective limit of compression and/or another length of each of the outer tube parts, which length can be obtained by compression, preferably determines the respective first and second position. The connection device can be displaced in the longitudinal direction between the first position and the second position. A plurality of resting positions may be provided, at which the connection device does not change independently without the effect of external forces and maintains its relative position. The rigidities of the outer tube parts and/or other physical properties of the outer tube parts can be adapted correspondingly in order to make it possible for the connection device to remain in the respective resting position.

Provisions are made according to an especially preferred embodiment of the present invention for the longitudinal flexibility of the outer tube part, especially of the outer tube parts, to be greater than a longitudinal flexibility of the inner line, especially in the pulling direction. This embodiment is based on the discovery that the outer tube is mechanically coupled by the port connectors along with the inner line. The forces acting on the connection device in the longitudinal direction to displace same in the longitudinal direction also act indirectly on the inner line because of the above-mentioned coupling. However, the outer tube or its outer tube parts preferably have a higher mechanical flexibility, so that a displacement of the connection device relative to the inner line will take place without causing an at least considerable change in the length of the latter. This is especially true when the forces act on the inner line in the pulling direction. The longitudinal flexibility shall be preferably defined as the flexibility in the longitudinal direction.

Provisions are made according to another preferred embodiment of the present invention for each outer tube part to be designed in the manner of a folded tube with a plurality of ring folds that can be opened and folded up, and a plurality of the ring folds are opened and a plurality of the ring folds are folded up. The ring folds of a folded tube are preferably arranged one after another. Each ring fold is a cylindrical section with V-shaped, symmetrically, radially inwardly or outwardly directed jacket surfaces, which face away from one another in an opened state and are in contact with one another in a folded-up state. Due to a plurality of the ring folds of the outer tube being opened and a plurality of the ring folds being folded up, it is possible that the connection device of the outer tube is displaceable in the longitudinal direction relative to the inner line. Ring folds of, for example, one tube part open and other ring folds, for example, of the other outer tube part fold up during the longitudinal displacement of the connection device. It is thus guaranteed that the overall length of the outer tube and/or the inner volume of the outer tube remain unchanged. The advantages already explained above are thus obtained.

Another preferred embodiment of the present invention is characterized in that the flexibility of each of the ring folds to change over from an opened state into a folded-up state or vice versa is greater than a longitudinal flexibility of the inner line, especially in the pulling direction. Due to the flexibility of each ring fold or of the ring folds that are relevant for the compression and expansion of the outer tube being selected to be greater than a flexibility of the inner line, it is guaranteed that the connection device is displaceable relative to the inner line in the longitudinal direction without considerably affecting the length of the inner line and/or the overall length of the outer tube. Another preferred embodiment of the present invention is characterized therefore in that the connection device is arranged between the ring folds of the outer tube such that the connection device can be displaced in the longitudinal direction relative to the inner line by folding up ring folds of one outer tube part and opening ring folds of the other outer tube part. The length of the inner line can thus remain at least essentially unchanged. This preferably applies correspondingly to the overall length of the outer tube. Reference is analogously made to the above-mentioned explanations for the longitudinal flexibility of the inner line concerning the longitudinal flexibility in the pulling direction.

Provisions are made according to another preferred embodiment of the present invention for a water trap for receiving condensation water to be connected to the at least one branch. The water trap is preferably used to receive condensation water from the outer tube. Such water traps are sufficiently known from the state of the art. The branch is preferably designed and set up to connect the water trap as simply as possible. As an alternative, another medical device, for example, an anesthetic evaporator, may also be connected to the branch. The branch and/or the water trap may have a quick connection means for this.

Provisions are made according to another preferred embodiment of the present invention for the inner line to be at least essentially dimensionally stable in the longitudinal direction. In other words, the physical properties, especially the stability of the inner line, are selected to be such that the inner line is free from permanent changes in length under usual loads.

Provisions are made according to another preferred embodiment of the present invention for a ratio of the longitudinal rigidity of the inner tube to the longitudinal rigidity of the outer tube to be selected to be such that a force acting on the connection device and on the inner tube via the outer tube parts and port connectors coupled therewith brings about a longitudinal displacement of the connection device due to compression of one outer tube part and a corresponding expansion of the other outer tube part while the length of the inner tube is at least essentially maintained.

The longitudinal rigidity shall be defined as a resistance of the inner tube and of the outer tube to a deformation by a force acting in the longitudinal direction. To guarantee a displacement of the connection device, the longitudinal rigidity of the inner tube is greater, preferably markedly greater, than the longitudinal rigidity of the outer tube or the longitudinal rigidity of the outer tube parts of the outer tube. The longitudinal rigidity of the inner tube is especially preferably at least 1.5 times greater than the longitudinal rigidity of the outer tube or as the longitudinal rigidity of the outer tube parts. It can thus be guaranteed in an especially simple manner than the length of the inner tube will be at least essentially maintained during a longitudinal displacement of the connection device. The ratio of the rigidities may be selected to be even greater, for example, 2.

The inner line is especially preferably a cable. The cable may have an especially high longitudinal rigidity in the pulling direction, so that an especially simple embodiment of the ventilation tube unit is obtained with a cable as the inner line.

Provisions are made according to another preferred embodiment of the present invention for the inner line to be designed as an inner tube and each inner line port as an inner tube port, so that two tube ducts are formed. Thus, provisions are preferably made for the first tube duct to be formed within the inner tube and for the second tube duct to be formed between the outer tube and the inner tube. The outer tube and the inner tube therefore advantageously form a coaxial arrangement. Such a ventilation tube unit is especially compact. Two separate ventilation tube units are therefore not necessary between the ventilator and the mask for a ventilation circuit, but only one ventilation tube unit is necessary.

According to another preferred embodiment of the present invention, provisions are made for the ventilation tube unit to have an inner tube extending between the port connectors (end connectors), wherein each port connector is connected by a corresponding inner tube port to an end of the inner tube, and wherein the inner tube is arranged between the inner line and the outer tube in the radial direction, so that two tube ducts are formed. The inner line, the inner tube and the outer tube thus preferably form a coaxial arrangement. The inner line is preferably designed to determine and fix the length between the port connectors. The inner line may have a correspondingly adapted rigidity or flexibility for this. The flexibility of the inner tube and/or the flexibility of the outer tube is preferably greater than the flexibility of the inner line. The connection device of the outer tube and a certain section of the inner tube can thus especially advantageously be displaced in parallel and relative to the inner line in the longitudinal direction. This is especially advantageous if the outer tube and the inner tube are mechanically connected to one another, at least partially, in the radial direction in order to increase the resistance to a radial deformation of the outer tube and/or inner tube.

Another preferred embodiment of the present invention is characterized in that the inner tube is provided with a plurality of corrugations in the manner of a corrugated tube, which corrugations prevent a folding over between the corrugations due to their at least essentially constant radii. This embodiment of the inner tube is preferably used to form the inner line and/or to support the inner line in its function of making the length of the ventilation tube unit robust against the effect of external forces. Compression of the inner tube can be effectively prevented from occurring due to the constant radii of the corrugations of the corrugated tube. Such corrugated tubes can be embodied with a high longitudinal rigidity in an especially simple manner.

Another preferred embodiment of the present invention is characterized in that the inner tube is designed in the manner of the outer tube, and the branch of the inner tube is led through the outer jacket of the outer tube. This embodiment of the inner tube can therefore be defined preferably as an alternative to the above embodiment of the inner tube. An identical embodiment of the inner tube and outer tube offers the advantage that the respective connection devices of these tubes can be designed such that they are displaceable in parallel. Radial connection devices are preferably provided between the connection devices, so that both connection devices are displaceable in parallel by an external actuation. Such an embodiment of the ventilation tube unit is especially comfortable for practical use.

Another preferred embodiment of the present invention is characterized in that the water trap or an additional water trap is connected to the branch of the inner tube in order to collect the condensation water formed in the inner tube. The branch of the inner tube leading through the outer jacket of the outer tube can consequently lead to a separate water trap or to the same water trap. A separate water trap represents the advantage that the tube duct formed within the inner tube is uncoupled from a tube duct formed between the inner tube and the outer tube and is not coupled by the water trap. A common water trap offers the advantage that such an arrangement is especially compact.

According to another aspect of the present invention, the object mentioned in the introduction is accomplished by a ventilation system according to the present invention, comprising a ventilator for the mechanical ventilation of a patient, at least one ventilation tube unit with a water trap and with a ventilation mask, wherein the ventilation tube unit is formed and/or designed according to one of the above aspects. The ventilation system therefore has analogously the same advantages as they were explained in connection with the previous embodiments.

Further additional features of the present invention will appear from the description of the embodiment according to the present invention with the claims and/or the attached drawings. Embodiments according to the present invention may incorporate individual features or a combination of a plurality of features. The present invention will be described below without limitation of the general inventive idea on the basis of the exemplary embodiments with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
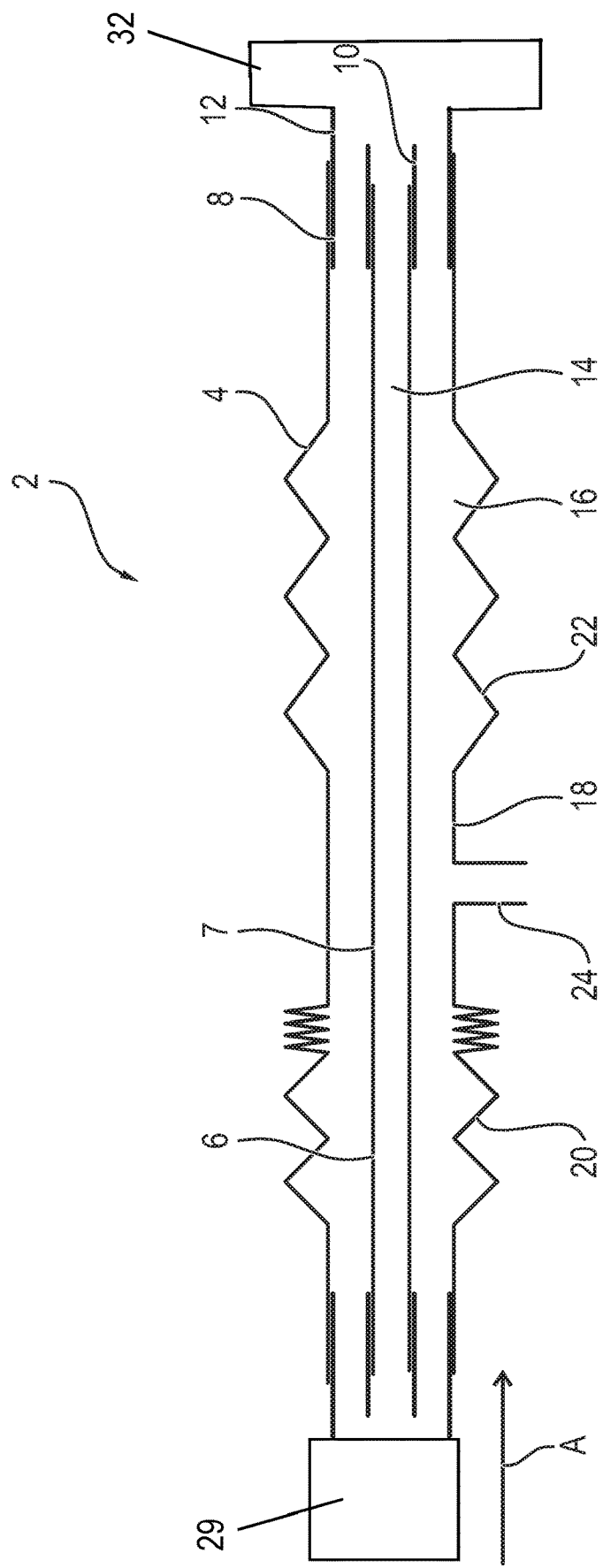
FIG. 1 is a sectional view of the ventilation tube unit in a first embodiment variant.

FIG. 1 shows a ventilation tube unit 2 according to the present invention in a sectional view, wherein the section is placed in the longitudinal direction A of the ventilation tube unit 2. The ventilation tube unit 2 may be part of a ventilation system. In addition to the ventilation tube unit 2, the ventilation system may include a ventilation mask 29 and a ventilator 32. The ventilation tube unit 2 comprises an outer tube 4, an inner line 6 and two port connectors 8. The inner line 6 is arranged within the outer tube 4, so that a coaxial arrangement is obtained from this. The inner line 6 and the outer tube 4 extend each between the outer port connectors 8. Each of the port connectors 8 has an inner line port 10 and an outer line port 12. One end of the inner line 6 is connected to the inner line port 10 and an end of the outer tube 4, which end is located on the same side, is connected to the outer line port 12. The opposite ends of the inner line 6 and of the outer tube 4 are connected to the other port connectors 8, namely in a corresponding way.

The inner line 6 is designed in FIG. 1 as an inner tube 7. The port connectors 8, the inner tube 7 and the outer tube 4 are designed due to their coaxial arrangement such that two tube ducts, namely, an inner tube duct 14 and a middle tube duct 16 are formed. Each of the two tube ducts 14, 16 extends over the entire length of the ventilation tube unit 2. Furthermore, the two tube ducts 14, 16 are pneumatically uncoupled from one another.

The outer tube 4 has a tubular connection device 18, which is arranged between a first outer tube part 20 and a second outer tube part 22 of the outer tube 4. The outer tube parts 20, 22 can be connected to the connection device 18 in the usual way. As an alternative, provisions may be made for the outer tube 4 to be made in one piece, so that the connection device 18 forms an integral part. The ends of the outer tube parts 20, 22 that point away from the connection device 18 are connected to one of the port connectors 8 each.

The tubular connection device 18 has at least one jacket-side branch 24 for connecting a medical unit (not shown), especially a water trap. The branch 24 is used especially to drain off condensation water formed in the middle tube duct 16 to the outside and to keep this away from the lungs of the patient being ventilated. To effectively guarantee the draining off of the condensation water, it is advantageous if the branch 24 is arranged at the deepest point between the two port connectors 8. However, this is not always in the middle between the port connectors 8, but it may also be off-center depending on the vertical arrangement of the port connectors 8.

To make it possible to position the branch 24 and the connection device 18 as flexibly as possible between the port connectors 8, each of the outer tube parts 20, 22 comprises a variable length structure that is designed such that it has variable length between a compressed state and an expanded state. The half of the first outer tube part 20 facing the connection device 18 is compressed in FIG. 1. This can be seen especially from the fact that the first outer tube part 20 is a folded tube with a plurality of ring folds. The half of the first outer tube part 20 facing the connection device 18 has folded-up ring folds. The other ring folds of the first outer tube part 20 are opened. The first outer tube part 20 is thus in an at least partially compressed state. The second outer tube part 22 is likewise a folded tube with a plurality of ring folds, which are each opened. The second outer tube part 22 is therefore in an expanded state.

Due to the different states of the first outer tube part 20 and of the second outer tube part 22, the connection device 18 is displaceable relative to the inner tube 7 in the longitudinal direction A by a compression of the second outer tube part 22 and a corresponding expansion of the first outer tube part 20.

The inner tube 7 has no ring folds. The inner tube 7 is therefore preferably suitable for determining and fixing the length of the ventilation tube unit 2 and/or the length between the port connectors 8. The inner tube 7 preferably has a correspondingly high longitudinal rigidity for this. This is preferably selected to be so high that a force for displacing the connection device 18 is not sufficient to upset and/or compress the inner tube 7. The inner tube 7 is therefore essentially dimensionally stable in the longitudinal direction.

To make it possible that the connection device 18 will also remain at the deepest point reached by displacement, provisions are made for the connection device 18 to be able to be positioned in a plurality of resting positions without the effect of external forces. This is preferably guaranteed by the outer tube parts 20, 22 being designed as folded tubes. Each of the ring folds of such a folded tube has two stable states, namely, a state in which the respective ring fold is opened, and another stable state, in which the respective ring fold is folded up. A plurality of stable states, which can be set by displacing the connection device 18 at the outer tube parts 20, 22, are thus obtained. If the ring folds of the outer tube parts 20, 22 are in a stable state, the connection device 18 is in a resting position, which will be maintained without the effect of external forces.

Figure 2:
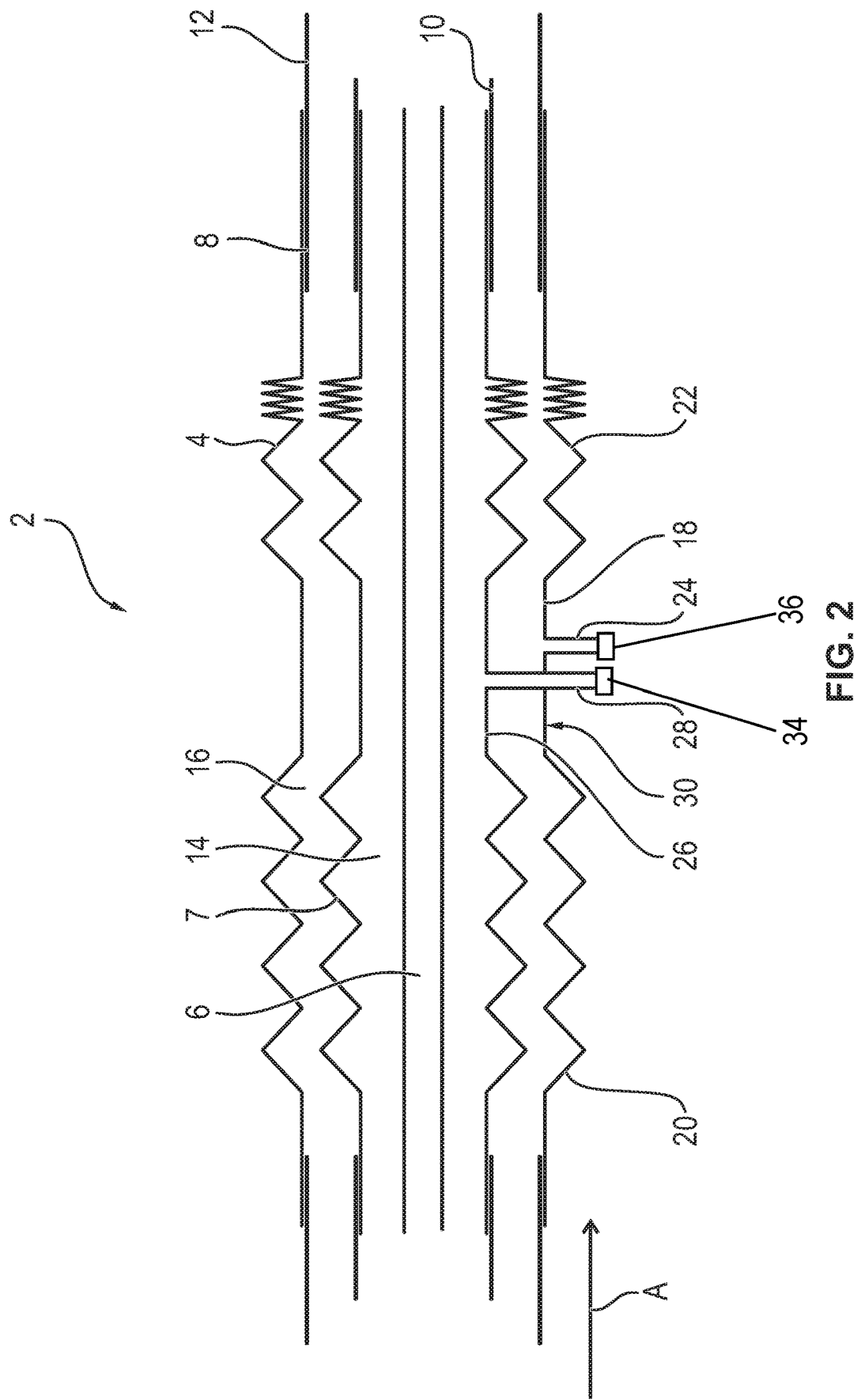
FIG. 2 is a sectional view of the ventilation tube unit in a second variant.

FIG. 2 shows another embodiment variant of the ventilation tube unit 2 according to the present invention, which has a plurality of features identical to those of the embodiment variant of the ventilation tube unit 2 explained above. If meaningful, reference will therefore be made here to the previous explanations given in connection with FIG. 1, and identical features are designated in FIG. 2 by the same reference numbers.

The ventilation tube unit 2 shown in FIG. 2 is characterized in that the inner line 6 is not formed by the inner tube 7. The inner line 6 is rather formed by a separate element. The inner tube duct 14 is formed therefore between the inner line 6 and the inner tube 7. The middle tube duct 16 is also formed, as before, between the inner tube 7 and the outer tube 4.

It is possible by means of this embodiment variant of the ventilation tube unit 2 that a connection device 26 of the inner tube 7 is displaced in the longitudinal direction in parallel to a connection device 18 of the outer tube 4, namely, relative to the inner line. It is thus possible that a branch 28 of the connection device 26 of the inner tube 7 is led through the outer jacket 30 of the outer tube 4. Separate water traps 34, 36 or a common water trap (not shown) can thus be connected to the branch 28 of the inner tube 7 and to the branch 24 of the outer tube 4 to collect the condensation water being formed in the inner tube and the outer tube. Each branch 24, 28 can be displaced in the longitudinal direction relative to the inner line 6 due to the corresponding connection device 18, 26 such that the respective branch 24, 28 is arranged at least essentially at the deepest point between the port connectors 8 and the ventilation tube unit 2. The condensation water being formed in the inner tube duct 14 and/or in the middle tube duct 16 can thus be removed from the ventilation system in an especially effective and reliable manner.

While specific embodiments of the invention have been shown and described in detail to illustrate the application of the principles of the invention, it will be understood that the invention may be embodied otherwise without departing from such principles.

The invention claimed is:

1. A ventilation tube unit for connection to a medical ventilator, the ventilation tube unit comprising:
   an outer tube comprising a first outer tube part, a second outer tube part and a tubular connection device comprising at least one jacket-side branch for connecting a medical unit, the connection device being arranged between the first outer tube part and the second outer tube part of the outer tube, the outer tube comprising an outer tube interior space defining at least a portion of a first fluid flow path;
   an inner line arranged within the outer tube, the inner line comprising an inner line interior space defining a second fluid flow path; and
   two port connectors, between which the outer tube and the inner line extend, wherein each of the port connectors is connected by a corresponding inner line port to one end of the inner line and by a corresponding outer tube port to an end of the outer tube, the end of the outer tube and the one end of the inner line being located on the same side, wherein each outer tube part comprises a variable length structure with a length that is variable between a compressed state and an expanded state, and the connection device is displaceable in a longitudinal direction relative to the inner line by compressing one outer tube part and correspondingly expanding the other outer tube part.

2. The ventilation tube unit in accordance with claim 1, wherein a longitudinal flexibility of the outer tube parts is greater than a longitudinal flexibility of the inner line in the longitudinal direction, each outer tube part extending about a portion of the first fluid flow path and a portion of the second fluid flow path.

3. The ventilation tube unit in accordance with claim 1, wherein each outer tube part comprises a folded tube with a plurality of ring folds that can be opened and folded up, wherein a portion of the plurality of ring folds are opened and a portion of the plurality of ring folds are folded up.

4. The ventilation tube unit in accordance with claim 3, wherein a flexibility of each of the plurality of ring folds to change over from an opened state into a folded-up state or vice versa is greater than a longitudinal flexibility of the inner line in the longitudinal direction.

5. The ventilation tube unit in accordance with claim 3, wherein the connection device is arranged between the plurality of ring folds of the outer tube such that the connection device is displaceable in the longitudinal direction relative to the inner line by folding up ring folds of one outer tube part and opening ring folds of the other outer tube part.

6. The ventilation tube unit in accordance with claim 1, wherein the medical unit is a water trap for receiving condensation water that is connected to the at least one jacket-side branch.

7. The ventilation tube unit in accordance with claim 1, wherein the inner line is dimensionally stable in the longitudinal direction.

8. The ventilation tube unit in accordance with claim 1, wherein a ratio of a longitudinal rigidity of the inner line to a longitudinal rigidity of the outer tube is selected to be such that a force acting on the connection device and via the outer tube parts and port connectors coupled therewith brings about a longitudinal displacement of the connection device by compression of one outer tube part and by a corresponding expansion of the other outer tube part while a length of the inner line is maintained.

9. The ventilation tube unit in accordance with claim 1, wherein the inner line is a cable.

10. The ventilation tube unit in accordance with claim 1, wherein the inner line is designed as an inner tube and each inner line port is designed as an inner tube port, so that two tube ducts are formed.

11. The ventilation tube unit in accordance with claim 10, wherein the inner tube comprises a corrugated tube with a plurality of corrugations, which prevent a folding over between the plurality of corrugations due to a constant radii.

12. The ventilation tube unit in accordance with claim 10, wherein a design of the inner tube is similar to a design of the outer tube, wherein a branch of the inner tube is led through an outer jacket of the outer tube.

13. The ventilation tube unit in accordance with claim 12, wherein the medical unit comprises a water trap or an additional water trap, the water trap or the additional water trap being connected to the branch of the inner tube in order to collect condensation water formed in the inner tube.

14. The ventilation tube unit in accordance with claim 1, further comprising an inner tube extending between the two port connectors, wherein the inner tube is arranged between the inner line and the outer tube in a radial direction, so that two tube ducts are formed.

15. The ventilation tube unit in accordance with claim 14, wherein the inner tube comprises a corrugated tube with a plurality of corrugations, which prevent a folding over between the plurality of corrugations due to a constant radii.

16. The ventilation tube unit in accordance with claim 14, wherein a design of the inner tube is similar to a design of the outer tube, wherein a branch of the inner tube is led through an outer jacket of the outer tube.

17. The ventilation tube unit in accordance with claim 16, wherein the medical unit comprises a water trap or an additional water trap, the water trap or the additional water trap being connected to the branch of the inner tube in order to collect condensation water formed in the inner tube.

18. A ventilation system, comprising:
a ventilator for mechanical ventilation of a patient;
a water trap;
a ventilation mask; and
a ventilation tube unit comprising:
an outer tube comprising a first outer tube part, a second outer tube part and a tubular connection device comprising at least one jacket-side branch connected to the water trap, the connection device being arranged between the first outer tube part and the second outer tube part of the outer tube, the outer tube comprising an outer tube inner space defining at least a portion of a first fluid flow path;
an inner line arranged within the outer tube, the inner line comprising an inner line inner space defining a second fluid flow path; and
two port connectors, between which the outer tube and the inner line extend, wherein each of the port connectors is connected by a corresponding inner line port to one end of the inner line and by a corresponding outer tube port to an end of the outer tube, the end of the outer tube and the one end of the inner line being located on the same side, wherein each outer tube part comprises a variable length structure with a length that is variable between a compressed state and an expanded state, and the connection device is displaceable in a longitudinal direction relative to the inner line by compressing one outer tube part and correspondingly expanding the other outer tube part.

19. The ventilation system in accordance with claim 18, wherein a longitudinal flexibility of the outer tube parts of the outer tube, is greater than a longitudinal flexibility of the inner line in the longitudinal direction, each outer tube part extending about a portion of the first fluid flow path and a portion of the second fluid flow path.

20. A medical ventilator method comprising the steps of:
providing a ventilation tube unit comprising:
an outer tube comprising a first outer tube part, a second outer tube part and a tubular connection device comprising at least one jacket-side branch connected to a water trap, the outer tube defining at least a portion of an outer tube fluid flow path, the connection device being arranged between the first outer tube part and the second outer tube part of the outer tube;
an inner line arranged within the outer tube, the inner line defining an inner line fluid flow path, the first outer tube part extending about at least one portion of the outer tube fluid flow path and at least one portion of the inner line fluid flow path, the second outer tube part extending about at least another portion of the outer tube fluid flow path and at least another portion of the inner line fluid flow path; and
two port connectors, between which the outer tube and the inner line extend, wherein each of the port connectors is connected by a corresponding inner line port to one end of the inner line and by a corresponding outer tube port to an end of the outer tube, the end of the outer tube and the one end of the inner line being located on the same side, wherein each outer tube part comprises a variable length structure with a length that is variable between a compressed state and an expanded state, and the connection device is displaceable in a longitudinal direction relative to the inner line by compressing one outer tube part and correspondingly expanding the other outer tube part;
displacing the connection device to one of a plurality of resting positions between a first position, in which the first outer tube part is fully compressed and a second position, in which the second other outer tube part is fully compressed, wherein the connection device maintains the one of a plurality of resting positions.

* * * * *